(12) United States Patent
Dvir (10) Patent No.: US 6,773,376 B2
(45) Date of Patent: Aug. 10, 2004

(54) SYSTEM AND METHOD FOR DERIVING ANGULAR ISOKINETIC MEASUREMENTS USING A LINEAR DYNAMOMETER

(75) Inventor: Zeevi Dvir, Hadera (IL)

(73) Assignee: Ramot At Tel Aviv University Ltd., Tel Aviv (IL)

( * ) Notice: Subject to any disclaimer, the term of this patent is extended or adjusted under 35 U.S.C. 154(b) by 155 days.

(21) Appl. No.: 10/278,066

(22) Filed: Oct. 23, 2002

(65) Prior Publication Data

US 2004/0082437 A1 Apr. 29, 2004

(51) Int. Cl.[7] .................................................. A61B 5/22
(52) U.S. Cl. ............................. 482/8; 482/9; 601/23; 73/379.01
(58) Field of Search ..................... 482/1–9, 900–902; 73/379.01–379.03; 601/1, 23, 24, 33–35

(56) References Cited

U.S. PATENT DOCUMENTS

| | | | |
|---|---|---|---|
| 3,465,592 A | | 9/1969 | Perrine |
| 4,148,479 A | | 4/1979 | Spector |
| 4,235,437 A | | 11/1980 | Ruis et al. |
| 4,563,004 A | | 1/1986 | Mattox |
| 4,628,910 A | | 12/1986 | Krukowski |
| 4,691,694 A | * | 9/1987 | Boyd et al. .................... 601/34 |
| 4,890,495 A | | 1/1990 | Slane |
| 4,907,797 A | | 3/1990 | Gezari et al. |
| 5,186,695 A | | 2/1993 | Mangseth et al. |
| 5,256,117 A | | 10/1993 | Potts et al. |
| 5,314,390 A | | 5/1994 | Westing et al. |
| 5,330,397 A | | 7/1994 | Prince et al. |
| 5,348,519 A | | 9/1994 | Prince et al. |
| 5,407,402 A | * | 4/1995 | Brown et al. ................... 482/4 |
| 5,421,798 A | | 6/1995 | Bond et al. |
| 5,437,587 A | | 8/1995 | Prince et al. |
| 5,722,937 A | * | 3/1998 | Smith ........................... 601/23 |

OTHER PUBLICATIONS

Reproducibility and validity of a new test protocol for measuring isokinetic trunk extension strength: Clinical Biomechanics, 16:627–630.
The identification of feigned isokinetic shoulder flexion weakness in normal subjects. American Journal of Physical Medicine and Rehabilitation 81:187–193, 2002.

* cited by examiner

Primary Examiner—Glenn E. Richman
(74) Attorney, Agent, or Firm—Mark M. Friedman

(57) ABSTRACT

A method for deriving isokinetic measurements of the moment applied by a body portion while the body portion performs a pivotal or flexing motion at a given angular velocity about an effective pivot axis. The method uses a linear dynamometer configured for performing isokinetic measurements over a predefined range of motion along a linear path. First, the linear dynamometer is deployed with its linear path substantially tangential to a circle of given radius about the effective pivot axis for measuring force applied by the body portion. The linear dynamometer is then used to measure a force profile applied by the body portion over a predefined range of motion at a predefined linear velocity. This force profile, the linear velocity and the radius are then used to derive data for the moment applied by the body portion and the corresponding angular velocity.

13 Claims, 6 Drawing Sheets

SYSTEM AND METHOD FOR DERIVING ANGULAR ISOKINETIC MEASUREMENTS USING A LINEAR DYNAMOMETER

FIELD AND BACKGROUND OF THE INVENTION

The present invention relates to isokinetic measurements and, in particular, it concerns a system and method for deriving angular isokinetic measurements using a linear dynamometer.

Muscle strength, which is the main parameter for estimation of muscle performance, can be measured in the context of two types of contraction: static and dynamic. During static contraction, the muscle does not move the joint since the external resistance matches the moment generated by the muscle. A value for muscle strength can thus, in principle, be obtained simply by using a load cell to measure this resistance. In practice, this approach is rarely used since the resulting value relates only to an isolated point in the range of motion and does not allow other important parameters to be determined.

Instead, the accepted technology for muscle strength determination employs isokinetic angular dynamometers which measure the moment exerted by a muscle during motion at a constant angular rate. Measurement of dynamic muscle strength has become one of the most important components in functional evaluation of patients primarily in the fields of orthopedics, rehabilitation and physiotherapy. Such measurements have also become very important for evaluation of damages and compensation in personal injury legal cases.

Devices for isokinetic exercise and therapy have been in use for many years. An early example is U.S. Pat. No. 3,465,592 to Perrine which discloses an isokinetic exercise system for both extension and flexion of a joint.

U.S. Pat. No. 4,235,437 to Ruis et al. discloses a robotic exercise machine which uses a computer to regulate the motion of an exercise arm in response to software programmed into the machine and in response to the force applied to the arm by the user as detected by a strain gauge at the end of the arm. By means of hydraulic cylinders and solenoid controlled valves, movement of the arm can be accurately controlled. However, the equipment provided in U.S. Pat. No. 4,235,437 is relatively complicated and requires expensive computer equipment and a complex linkage system. Further, because the equipment is computer controlled, the user must spend some time programming the computer with the desired settings before exercising. This, of course, is time consuming and detracts from the exercising.

It is to be appreciated that, with muscle exercise and rehabilitation apparatus, it is necessary that movement of the arm be smooth in all modes of operation. A problem with computer controlled apparatus is that the computer must make various samplings and computations, and thereafter makes corrections that are necessary. Although computer time is generally considered fast, the amount of time necessary for the computer to perform such operations and then control the mechanical and hydraulic devices of the apparatus may not result in smooth movement of the exercise arm, particularly at small loads.

Further, with hydraulic systems, such as that shown in the above U.S. patent, various problems of leakage, dirt in the servo valves, compliance in the hoses and pipes and heat dissipation result which detract from the accuracy of the system.

Representative of more modern systems currently in widespread use is U.S. Pat. No. 4,628,910 to Krukowski (Biodex Corp.). Such systems provide accurate measurements for concentric, and in some cases also eccentric, movements for a range of different joints. The complexity of the systems render them bulky and very costly.

The systems in widespread use typically take measurements over substantially the full range of mobility of the joint in question. Recently, research has indicated that measurements taken over a relatively small angular range in fact give results very similar to those taken over larger angular ranges. Examples of articles indicative of this finding include: Dvir Z., Keating J., The reproducibility of isokinetic trunk extension: A study using very short range of motion. *Clinical Biomechanics* 16:627–630, 2001; and Dvir Z., Steinfeld-Cohen, Y., Peretz, C., The identification of feigned isokinetic shoulder flexion weakness in normal subjects. *American Journal of Physical Medicine and Rehabilitation* 81:187–193, 2002. These findings have not previously been used to in any way simplify the measurement systems in use.

Finally, it should be noted that various implementations of linear dynamometers, including linear isokinetic dynamometers, have been developed. These linear dynamometers are typically used in devices for highly specific exercises, such as push-pull motions (e.g., U.S. Pat. No. 4,890,495), pedaling motions (e.g., U.S. Pat. No. 5,330,397) or lifting (e.g., U.S. Pat. No. 5,186,695). None of these devices are able to measure the angular isokinetic measurements which are required for muscle strength evaluations as described above.

There is therefore a need for a system and method for deriving angular isokinetic measurements which would be rendered simpler and more economical by employing a relatively small range of motion. It would also be advantageous to provide a system and method for deriving angular isokinetic measurements using a linear dynamometer.

SUMMARY OF THE INVENTION

The present invention is a system and method for deriving angular isokinetic measurements using a linear dynamometer.

According to the teachings of the present invention there is provided, a method for deriving isokinetic measurements of the moment applied by a body portion while the body portion performs a pivotal or flexing motion at a given angular velocity, the motion having an effective pivot axis, the method comprising: (a) providing a linear dynamometer configured for performing isokinetic measurements over a predefined range of motion along a linear path; (b) deploying the linear dynamometer for measuring force applied by the body portion, the dynamometer being positioned with its linear path substantially tangential to a circle of given radius about the effective pivot axis; (c) measuring by use of the linear dynamometer a force profile applied by the body portion over a predefined range of motion at a predefined linear velocity; and (d) using the force profile, the linear velocity and the radius to derive data for the moment applied by the body portion and the corresponding angular velocity.

According to a further feature of the present invention, the measuring is performed concentrically. According to an alternative, or additional, feature of the present invention, the measuring is performed eccentrically.

According to a further feature of the present invention, the measuring is performed at two different linear velocities, corresponding to two different angular velocities of the body portion about the effective pivot axis.

According to a further feature of the present invention, the predefined range of motion and the radius are chosen such that a corresponding range of angular motion of the body portion is less than 30°, and preferably no more than about 20°.

The method of claim 1, wherein the predefined range of motion is at least about 25 mm, and preferably between about 5 cm and about 15 cm.

There is also provided according to the teachings of the present invention, a system for deriving isokinetic measurements of the moment applied by a body portion of a subject while the body portion performs a pivotal or flexing motion at a given angular velocity, the motion having an effective pivot axis, the system comprising: (a) a linear dynamometer having a housing and a displacement portion, the linear dynamometer being configured for measuring a force applied to the displacement portion along a line of action while the displacement portion undergoes isokinetic linear motion along the line of action relative to the housing; (b) a chair for supporting the subject in a predefined position; and (c) an adjustable support system for supporting the linear dynamometer and the chair, the adjustable support system being configured to allow selective fixing of the linear dynamometer at any of a plurality of vertical positions over a given range of vertical displacement relative to the chair, and at any of a plurality of angular positions within a given range of angular positions about a substantially horizontal adjustment axis.

According to a further feature of the present invention, the adjustable support system is further configured to allow selective fixing of relative positions of the linear dynamometer and the chair within a predefined range of relative displacement in two degrees of freedom of horizontal displacement.

According to a further feature of the present invention, the predefined range of relative displacement in two degrees of freedom of horizontal displacement is defined by a system of rails supporting the chair.

According to a further feature of the present invention, the adjustable support system is further configured to allow rotation of the chair about a substantially vertical axis passing through the chair.

According to a further feature of the present invention, the adjustable support system is further configured to allow tilting of the chair about a substantially horizontal axis.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a system and method for deriving angular isokinetic measurements using a linear dynamometer.

The principles and operation of systems and methods according to the present invention may be better understood with reference to the drawings and the accompanying description.

Figure 1:
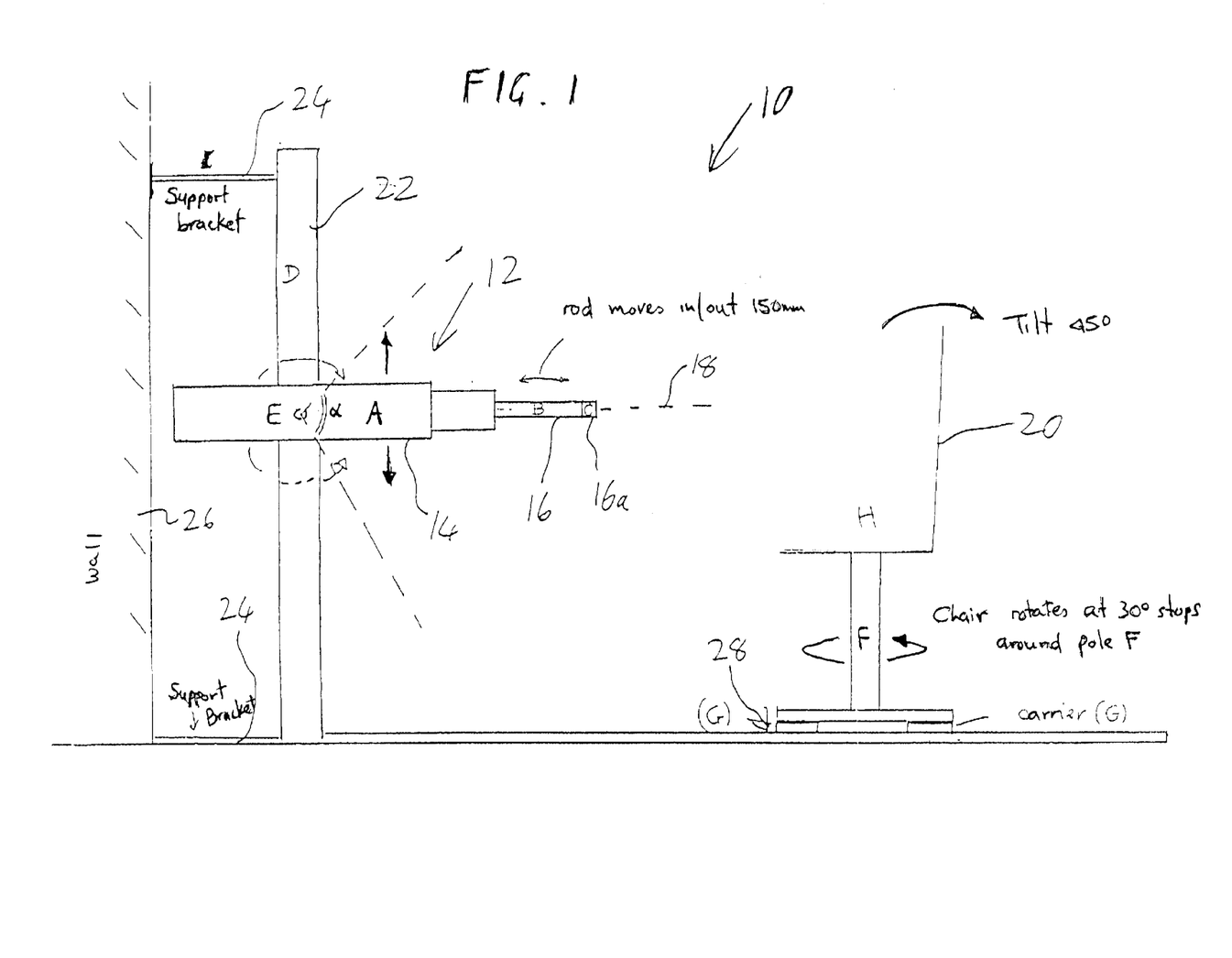
FIG. 1 is a schematic side view of a preferred implementation of a system for deriving angular isokinetic measurements using a linear dynamometer, constructed and operative according to the teachings of the present invention.
Figure 3:
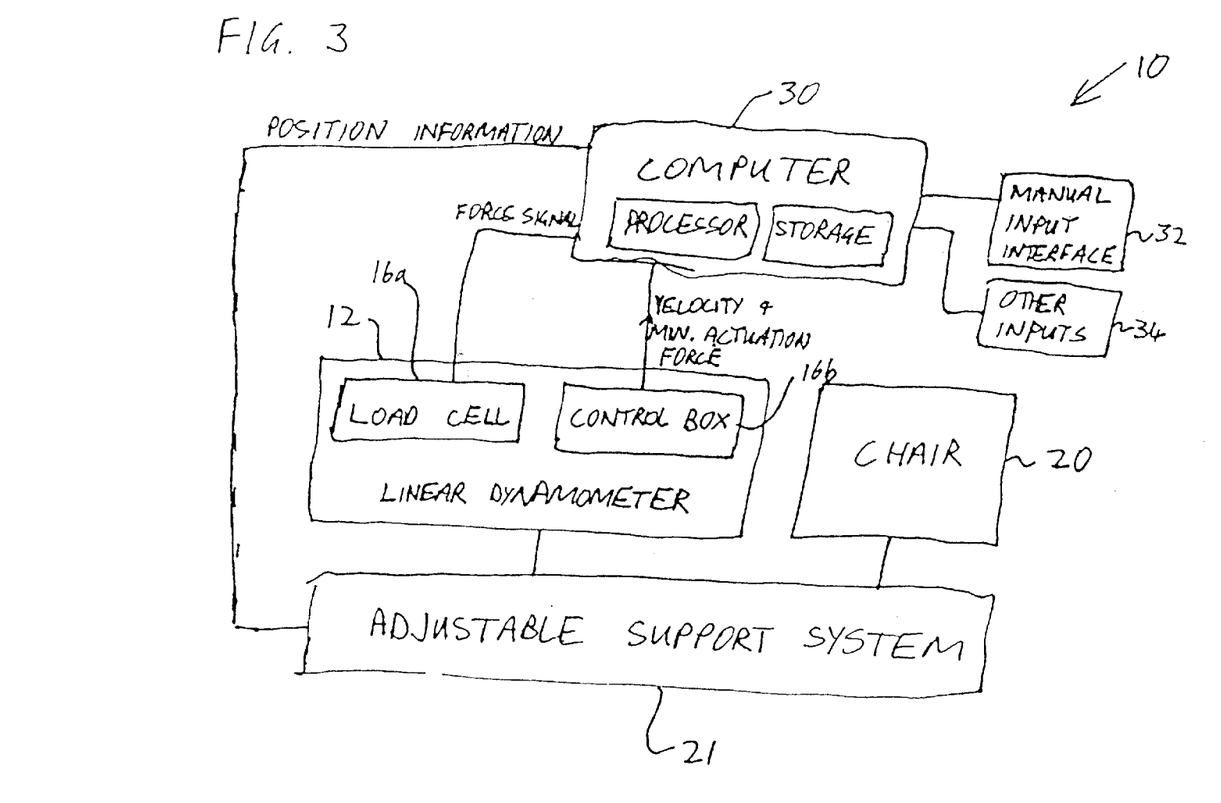
FIG. 3 is a schematic block diagram of the system of claim 1.

Referring now to the drawings, FIGS. 1 and 3 show a system, generally designated 10, constructed and operative according to the teachings of the present invention, for deriving isokinetic measurements of the moment applied by a body portion of a subject while the body portion performs a pivotal or flexing motion at a given angular velocity.

Generally speaking, the present invention is based upon the aforementioned observation that measurements taken over a relatively small angular range in fact give results very similar to those taken over larger angular ranges. In view of this observation, the present invention approximates a short arc of the required angular motion by linear motion. In practice, in this type of application, it has been found that a straight path is an acceptable approximation to a circular motion over a range of up to about 20°, or in some cases even 30°. This allows great simplification of both the dynamometer itself and the overall device structure.

Thus, referring more specifically to the method of the present invention, there is provided a method for deriving isokinetic measurements of the moment applied by a body portion while the body portion performs a pivotal or flexing motion at a given angular velocity about an effective pivot axis. The method uses a linear dynamometer configured for performing isokinetic measurements over a predefined range of motion along a linear path. First, the linear dynamometer is deployed with its linear path substantially tangential to a circle of given radius about the effective pivot axis for measuring force applied by the body portion. The linear dynamometer is then used to measure a force profile applied by the body portion over a predefined range of motion at a predefined linear velocity. This force profile, the linear velocity and the radius are then used to derive data for the moment applied by the body portion and the corresponding angular velocity.

It will be noted that the technique described herein employs a linear dynamometer to provide individual muscle group performance parameters. This stands in clear contrast to the aforementioned conventional linear devices which provide only overall performance information relating to multiple muscle groups from which information of this type cannot readily be derived.

In order to remain within a range of movement where a straight motion is an acceptable approximation for an arcuate path, the predefined range of motion and the radius are preferably chosen such that a corresponding range of angular motion of the body portion is less than 30°, and more preferably no more than about 20°.

In a preferred implementation illustrated here, system 10 has a linear dynamometer 12 having a housing 14 and a displacement portion 16. Dynamometer 12 is configured for measuring a force applied to displacement portion 16 along a line of action 18 while displacement portion 16 undergoes isokinetic linear motion along line of action 18 relative to housing 14. System 10 also includes a chair 20 for supporting a subject in a predefined position, and an adjustable support system for supporting the linear dynamometer and the chair. The adjustable support system, represented schematically in FIG. 3 as box 21, is configured to provide various degrees of freedom to adjust the relative positions of the dynamometer and the subject so that the line of action of the dynamometer corresponds substantially to a tangent of the angular motion of the joint in question. Other components of system 10 typically include a computer 30 with an interface 32 for manual entry of parameters and/or a number of other inputs 34.

Turning now to the features of system 10 in more detail, it should be noted that the adjustable support system 21 need not be a single structure which supports both dynamometer 12 and chair 20 directly. Thus, in the example of support system 21 shown here, dynamometer 12 is supported on a pillar 22 which is clamped via brackets 24 to a fixed external surface such as a wall 26, while chair 20 is supported on a floor-mounted system of rails 28 which may or may not be directly connected to pillar 22. Furthermore, it should be noted that the subdivision of adjustments between the dynamometer and the chair is typically not critical. Thus, for example, vertical adjustment may be achieved either by providing an up-down adjustment for dynamometer 12 or by providing such an adjustment for chair 20, so long as the required range of relative vertical adjustment is provided.

Preferably, the support system is configured to allow selective fixing of the linear dynamometer at any of a plurality of vertical positions over a given range of vertical displacement relative to the chair, and at any of a plurality of angular positions within a given range of angular positions about a substantially horizontal adjustment axis. In the example shown here, these two adjustments are implemented by appropriate adjustable mounting of dynamometer 12 on pillar 22. Mechanical solutions for allowing fixing of an element at a required height and angle on a vertical support are numerous, and will not be presented here in detail. Clearly, the adjustment mechanism may be continuous within a given range, or may define a plurality of distinct defined clamping positions and/or angles. In certain cases, in order to achieve high clamping rigidity without use of sophisticated components, discrete clamping positions and angles may be typically preferred.

A typical range of vertical relative motion between dynamometer 12 and chair 20 is preferably about 100 cm. For a fixed height chair of typical height, the range of heights for the dynamometer preferably starts from no more than about 20 cm from the underlying surface. With regard to the angle of inclination about the horizontal axis, this adjustment preferably provides a range of angles spanning at least about 120°, and more preferably at least about 150°. In the implementation shown here, dynamometer 12 is at a fixed orientation about a vertical axis, rotation being more effectively provided by rotation of the chair as will be described below.

The support system is preferably additionally configured to allow selective fixing of relative positions of the linear dynamometer and the chair within a predefined range of relative displacement in two degrees of freedom of horizontal displacement. This adjustment is here provided by the aforementioned system of rails 28. The range of motion provided by the system of rails is preferably at least about a meter, and preferably about 1.2 meters forwards and rearwards (i.e., towards and away from dynamometer 12), and about 40 cm sideways.

The support system is preferably further configured to allow rotation of the chair about a substantially vertical axis passing through the chair. Most preferably, this is implemented as a 360° rotatable connection above system of rails 28, with predefined clamping positions at angular intervals of no more than about 30°.

Figure 4A:
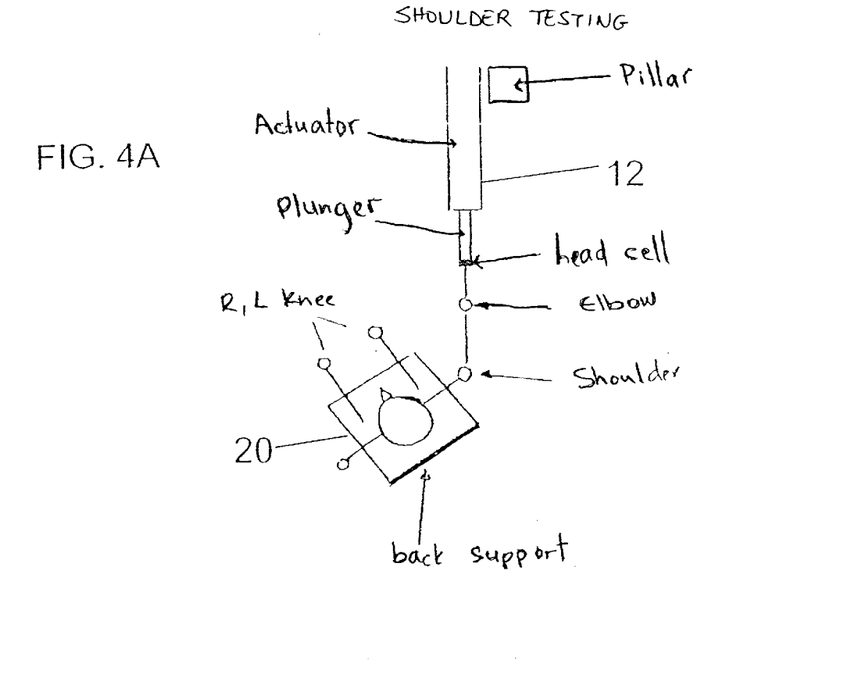
FIGS. 4A and 4B are schematic plan and isometric views, respectively, illustrating the use of the system of FIG. 1 to perform shoulder elevation testing.
Figure 4B:
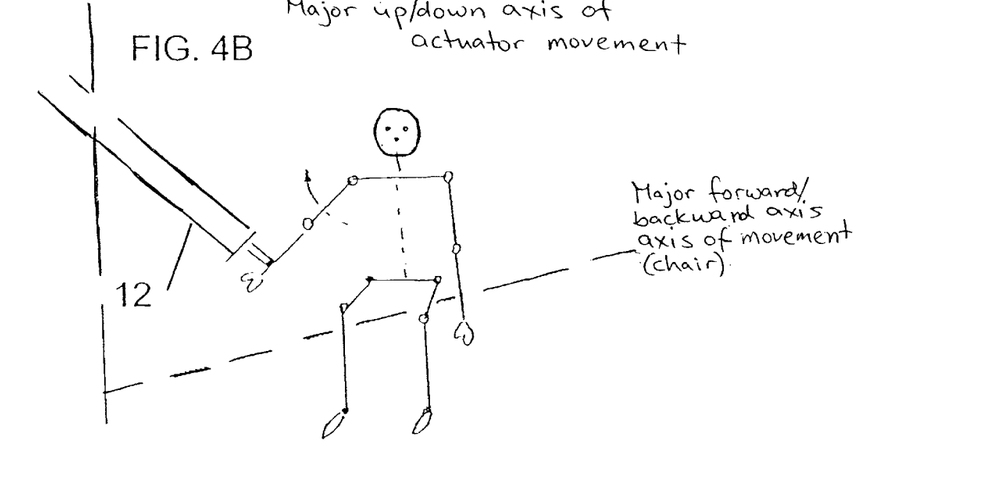

It will be appreciated that the various adjustments described thus far facilitate alignment of dynamometer 12 for performing measurements on substantially any body portion in substantially any required direction. By way of a first example, FIGS. 4A and 4B show the system adjusted for obtaining shoulder lifting measurements. In this case, as seen in the plan view of FIG. 4A, the chair is rotated anticlockwise and moved slightly to the left to bring the line of action of dynamometer 12 into the plane swept by the arm during lifting action of the shoulder. The distance between dynamometer 12 and chair 20, as well as the angle of inclination of dynamometer 12 are then adjusted to bring the dynamometer into the required perpendicular relation to the arm of the subject prior to measurement.

Figure 5A:
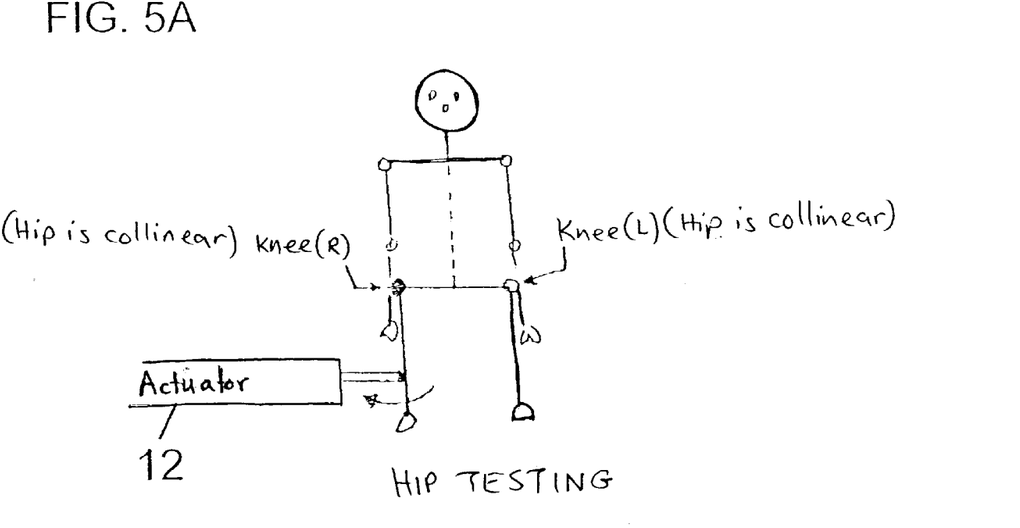
FIGS. 5A and 5B are schematic front and isometric views, respectively, illustrating the use of the system of FIG. 1 to hip rotation testing.
Figure 5B:
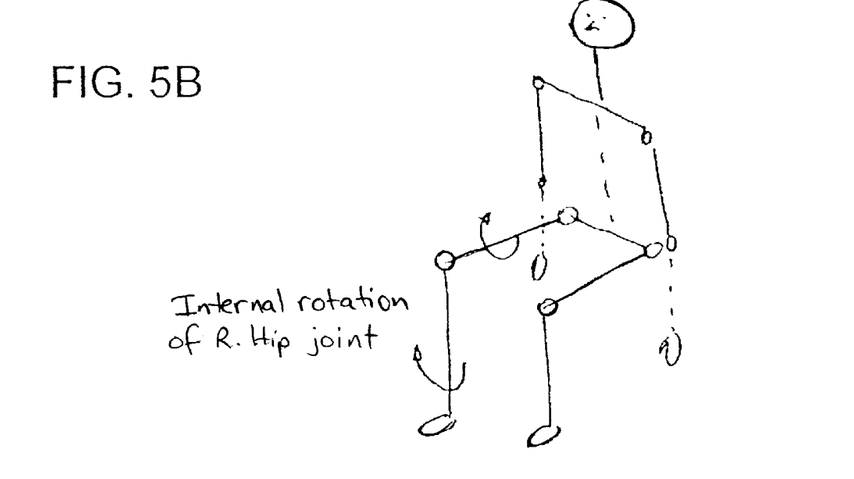

In a further example illustrated in FIGS. 5A and 5B, shows deployment of the system for measurement of internal rotation of the right hip joint. In this case, chair 20 is turned and displaced relative to dynamometer 12 so that the dynamometer is aligned laterally with the subject's leg. The dynamometer is then lowered and leveled to a position perpendicular to, and in contact with, the subject's lower leg, as shown.

Figure 2:
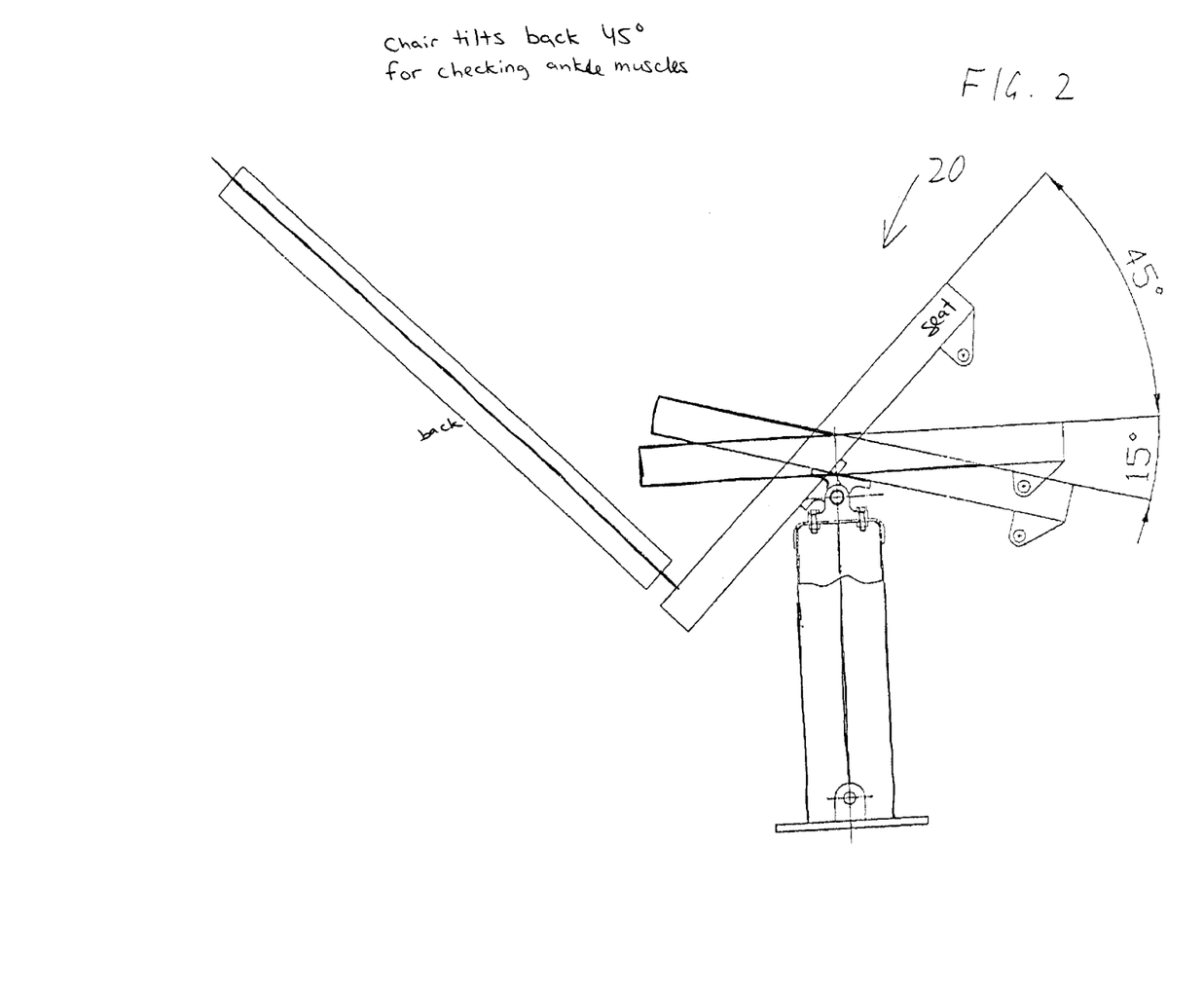
FIG. 2 is a schematic side view of a chair for use as part of the system of FIG. 1.

According to a further option, the support system is further configured to allow tilting of the chair about a substantially horizontal axis, for example as illustrated in FIG. 2. In the example shown here, the chair allows a reclining tilt of up to about 45°. This is particularly useful to complement the tilting of the dynamometer to facilitate measurements on muscles in the ankle or foot. The implementation illustrated here also provides a forward tilt of up to about 15°.

Figure 6:
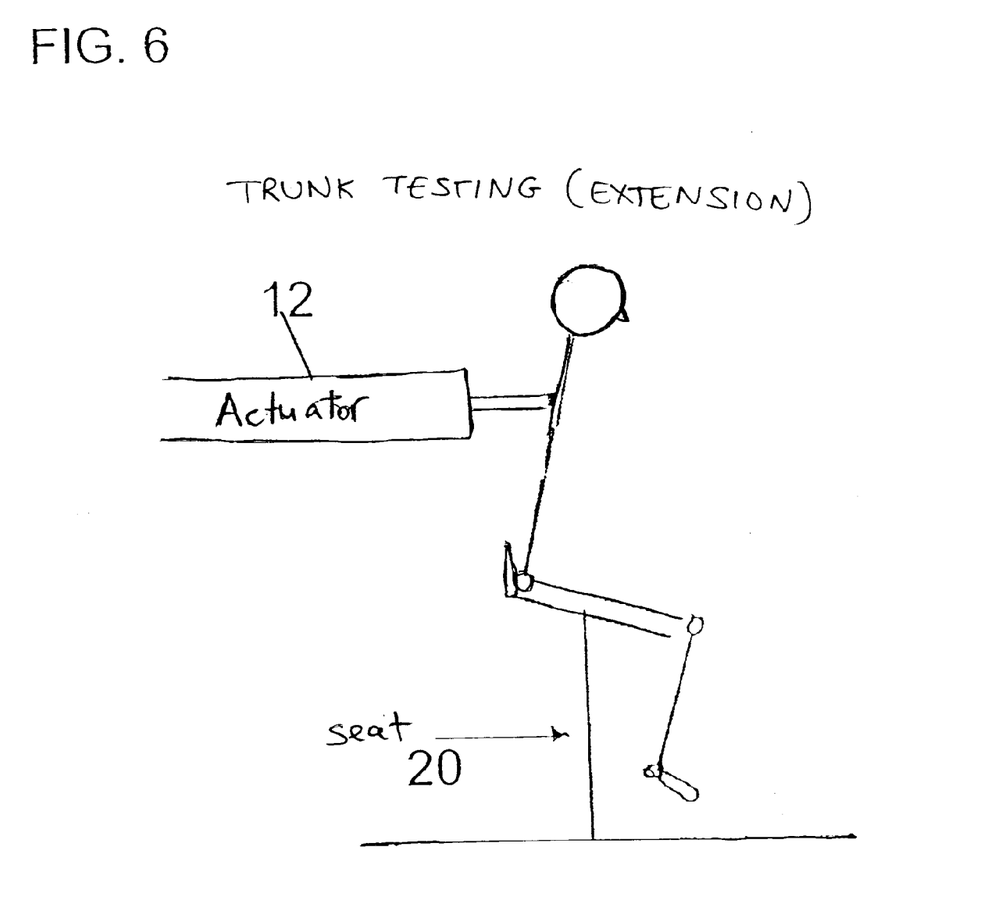
FIG. 6 is a schematic side view illustrating the use of the system of FIG. 1 to trunk extension testing.

FIG. 6 illustrates an application employing the forward tilt of chair 20 to perform trunk extension testing. In this case, the subject faces away from the dynamometer and measurements are taken while the subject pushes backwards against the dynamometer. The forward tilt of the chair has been found to be advantageous since it effectively opens up the angle between the thigh and the pelvis (the "hip flexion angle") which is important during back testing. To facilitate access to the subject's back, chair 20 may optionally be configured to allow temporary replacement of a backrest by a lumbar buttress.

Although only a limited number of testing positions have been illustrated here, it will be clear to one ordinarily skilled in the art that these examples may be generalized to substantially any movement of a body part associated with a group of muscles.

Turning now to features of dynamometer 12, this may be any conventional type of linear dynamometer. Typically, an electronically actuated linear dynamometer is used. Measurements are typically sensed by a load cell 16a mounted at the end of displacement portion 16. The dynamometer is preferably designed to allow both concentric measurements, i.e., where the motion is in the same direction as the force applied by the subject, and/or eccentric measurements, i.e., where the force applied by the subject opposes motion induced by the actuator of the dynamometer.

The dynamometer typically includes its own control unit 16b (FIG. 3) which may be located within the actuator housing or as a separate control box. Control unit 16b preferably allows selection of parameters such as velocity and minimum required actuation force, as well as selection of concentric or eccentric modes, where available. Alternatively, control of the dynamometer may be integrated as additional functions performed by computer 30.

In many cases, it is useful to take measurements at two or more different linear velocities, corresponding to two different angular velocities of the body portion about the effective pivot axis. This may be implemented simply by appropriate design and setting of the dynamometer. It will be appreciated that the system of the present invention may also be used to make measurements in a number of other modes, such as static or constant force measurements.

For most implementations of the present invention, a linear range of movement for dynamometer 12 of about 15 cm is sufficient. The actual length of motion used for each measurement is set by the practitioner prior to use. In order to achieve isokinetic conditions, measurements are preferably performed over a range of at least about 25 mm. In most cases, the predefined range of motion for measurements between about 5 cm and about 15 cm.

Turning now to computer 30, this may be a standard PC operating under suitable software, or a dedicated hardware system, or firmware, as is known in the art. Computer 30 receives the force information from load cell 16a. Information regarding the joint and type of motion being tested, and the distance from the effective axis of rotation to the point of contact with the dynamometer are typically input manually via interface 32. Alternatively, this information may be derived automatically or semi-automatically by use of various displacement sensors and/or image processing video systems. In most cases, the simple manual input option is considered sufficient.

In general, the aforementioned information (namely, type of test performed, distance from axis to load cell, and load cell force information) are fully sufficient to allow computer 30 to construct the force-distance curve, and hence to derive any required parameters. In many cases, however, it is preferable to store with the results with various additional data. Specifically, dynamometer control data defining settings used for the test (e.g., velocity, minimum actuation force) are preferably provided to computer 30 from control box 16b. Furthermore, in order to ensure repeatability of the test layout, it is preferable to store position information data indicative of the exact positions of the dynamometer and the chair during the test. Optionally, this data may be output automatically from encoders (not shown) associated with adjustable support system 21. Finally, the test results may optionally be combined with other patient data and/or diagnostic information from other tests input via interface 32 or from other systems via inputs 34. The results may be displayed or otherwise output in any known form including, but not limited to, temporary visual display, printed copies, or computer files recorded on magnetic media or CD. The output devices are not described here, but will be fully understood by one ordinarily skilled in the art.

The operation of system 10 will now be clearly understood. Specifically, the practitioner positions a subject in chair 20 and adjusts chair 20 and dynamometer 12 linearly and angularly until line of action 18 corresponds substantially to a tangent to the arcuate motion of the limb about the joint in question, with line of action 18 substantially perpendicular to the part of the limb distal to the joint. The subject is then instructed to push against the load cell 16a while dynamometer 12 is actuated to perform the required concentric and/or eccentric measurements. Computer 30 then processes the measurements to derive the corresponding angular muscle strength values and/or any other required parameters.

It will be appreciated that the above descriptions are intended only to serve as examples, and that many other embodiments are possible within the spirit and the scope of the present invention.

What is claimed is:

1. A method for deriving isokinetic measurements of the moment applied by a body portion while the body portion performs a pivotal or flexing motion at a given angular velocity, the motion having an effective pivot axis, the method comprising:
   (a) providing a linear dynamometer configured for performing isokinetic measurements over a predefined range of motion along a linear path;
   (b) deploying the linear dynamometer for measuring force applied by the body portion, the dynamometer being positioned with its linear path substantially tangential to a circle of given radius about the effective pivot axis;
   (c) measuring by use of the linear dynamometer a force profile applied by the body portion over a predefined range of motion at a predefined linear velocity; and
   (d) using the force profile, the linear velocity and the radius to derive data for the moment applied by the body portion and the corresponding angular velocity.

2. The method of claim 1, wherein said measuring is performed concentrically.

3. The method of claim 1, wherein said measuring is performed eccentrically.

4. The method of claim 1, wherein said measuring is performed at two different linear velocities, corresponding to two different angular velocities of the body portion about the effective pivot axis.

5. The method of claim 1, wherein the predefined range of motion and the radius are chosen such that a corresponding range of angular motion of the body portion is less than 30°.

6. The method of claim 1, wherein the predefined range of motion and the radius are chosen such that a corresponding range of angular motion of the body portion is no more than about 20°.

7. The method of claim 1, wherein the predefined range of motion is at least about 25 mm.

8. The method of claim 1, wherein the predefined range of motion between about 5 cm and about 15 cm.

9. A system for deriving isokinetic measurements of the moment applied by a body portion of a subject while the body portion performs a pivotal or flexing motion at a given angular velocity, the motion having an effective pivot axis, the system comprising:
   (a) a linear dynamometer having a housing and a displacement portion, said linear dynamometer being configured for measuring a force applied to said displacement portion along a line of action while said displacement portion undergoes isokinetic linear motion along said line of action relative to said housing;
   (b) a chair for supporting the subject in a predefined position; and
   (c) an adjustable support system for supporting said linear dynamometer and said chair, said adjustable support system being configured to allow selective fixing of said linear dynamometer at any of a plurality of vertical positions over a given range of vertical displacement relative to said chair, and at any of a plurality of angular positions within a given range of angular positions about a substantially horizontal adjustment axis.

10. The system of claim 9, wherein said adjustable support system is further configured to allow selective fixing of relative positions of said linear dynamometer and said chair within a predefined range of relative displacement in two degrees of freedom of horizontal displacement.

11. The system of claim 10, wherein said predefined range of relative displacement in two degrees of freedom of horizontal displacement is defined by a system of rails supporting said chair.

12. The system of claim 9, wherein said adjustable support system is further configured to allow rotation of said chair about a substantially vertical axis passing through said chair.

13. The system of claim 9, wherein said adjustable support system is further configured to allow tilting of said chair about a substantially horizontal axis.

* * * * *